United States Patent [19]

Childs

[11] 4,262,146

[45] Apr. 14, 1981

[54] PRODUCTION OF ALIPHATIC ETHERS

[75] Inventor: William V. Childs, Bartlesville, Okla.

[73] Assignee: Phillips Petroleum Company, Bartlesville, Okla.

[21] Appl. No.: 112,266

[22] Filed: Jan. 15, 1980

[51] Int. Cl.³ .............................................. C07C 43/04
[52] U.S. Cl. ..................................... 568/697; 422/188; 260/692
[58] Field of Search .......................... 568/697; 260/692

[56] References Cited

U.S. PATENT DOCUMENTS

| 3,037,063 | 5/1962 | Harper | 260/700 |
|---|---|---|---|
| 3,324,164 | 6/1967 | Merkel et al. | 260/700 |
| 4,039,590 | 8/1977 | Ancillotti et al. | 568/697 |
| 4,071,567 | 1/1978 | Ancillotti et al. | 568/697 |

FOREIGN PATENT DOCUMENTS

| 863977 | 8/1978 | Belgium . | |
| 2911077 | 10/1979 | Fed. Rep. of Germany | 568/697 |

OTHER PUBLICATIONS

Obenaus et al., "The New and Versatile Huls-Process to Produce the Octane Improving MTBE," Paper No. 1303, Philadelphia Meeting AIChe, 1978.

Primary Examiner—Joseph E. Evans

[57] ABSTRACT

A process is disclosed for the reaction of alcohols and iso-olefins to produce ethers wherein two reactors connected in series are employed and portions of the iso-olefin feed are diverted from said first reactor to said second as required to assist in maintaining the temperature in the first reactor below a selected valve. A system for achieving that end is also disclosed.

15 Claims, 1 Drawing Figure

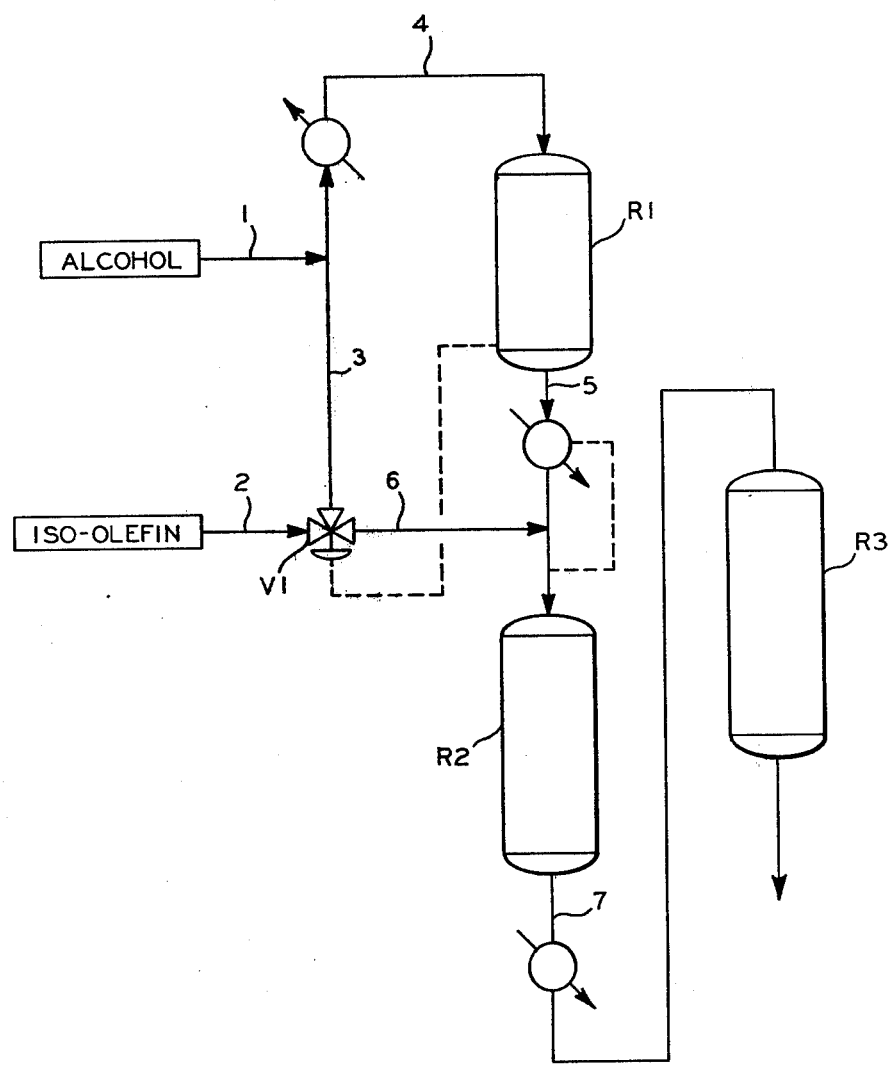

PRODUCTION OF ALIPHATIC ETHERS

This invention relates to the production of aliphatic ethers by the catalytic reaction of iso-olefins with alcohols.

It is well known that aliphatic ethers can be formed by reacting an iso-olefin and alcohol in the presence of an acid ion exchange resin. The reaction is exothermic and it is necessary to limit the temperature rise within the reaction zone. If the temperature gets too high, oligomerization occurs thus reducing the selectivity and deactivating the catalyst.

One technique typically used for controlling the temperature in the reaction zone involves cooling part of the effluent and recycling the cooled effluent through the reaction zone. This technique requires a pump with its associated utility and maintenance costs.

Another technique used for controlling the temperature involves the use of staged reactors with interstage cooling. In this technique, the temperature in the first reaction zone is controlled by limiting iso-olefin conversion by using high space velocities in the first reaction zone. Obviously, such a process does not make optimum use of the reaction zones, since reaction is being purposefully limited in at least one of the reactors.

An object of the present invention is to provide an improved method for controlling temperature in the etherification reaction.

Another object of the present invention is to provide an etherification process having improved resistance to having the catalyst deactivated through oligomer formation.

Still another object of this invention is to provide a system for reducing the maintenance and utility expenses involved in controlling the temperature of an etherification reaction.

Other aspects, objects, and advantages will be apparent to those skilled in the art from the following description and the attached drawing wherein FIG. 1 is a schematic illustration of a preferred embodiment of the process of the instant invention.

The instant invention involves an improvement in an etherification process wherein (1) a first feedstream containing alcohol and a second feedstream containing iso-olefin are passed through a first reaction zone containing acid ion exchange resin under conditions such that iso-olefin is converted to aliphatic ether and (2) effluent from that first reaction zone is passed through a second reaction zone containing acid ion exchange resin under conditions such that iso-olefin is converted to aliphatic ether. The improvement comprises diverting portions of said second feedstream to said second reaction zone in response to the temperature of said first reaction zone as required to assist in maintaining the maximum temperature in said first reaction zone below a selected value.

The iso-olefins which may be employed in the present invention include any of those which are readily converted to ethers by reaction with primary or secondary alcohols in the presence of the acid ion exchange resin catalyst. Generally, that includes those iso-olefins having 4 to 16 carbon atoms per molecule. Examples of such iso-olefins include isobutylene, isoamylene, isohexylene, isoheptylene, isooctylene, isononylene, isodecylene, isoundecylene, isododecylene, isotridecylene, isotetradecylene, isopentadecylene, and isohexadecylene, or mixtures of two or more thereof.

The alcohols which may be utilized include the primary and secondary aliphatic alcohols of from 1 to 12 carbon atoms, such as methanol, ethanol, propanol, isopropanol, the primary and secondary butanols, pentanols, hexanols, ethylene glycol, propylene glycol, butylene glycol, the polyglycols, and glycerol, etc., or mixtures of two or more thereof.

The presently preferred reactants are methanol and isobutylene because they yield methyl tertiary butyl ether (MTBE) which has utility as an octane improver for gasoline. Accordingly, it is currently preferred for the iso-olefins to be predominately isobutylene and the alcohols predominately methanol. Even more preferably the iso-olefins consist essentially of isobutylene and the alcohols consist essentially of methanol.

It is generally preferred for the iso-olefin and the alcohol to be passed through the reaction zones in the presence of diluents which do not have an adverse effect upon the etherification reaction. The diluents can be present in either the first stream or the second stream, or both, preferably the diluent is in the iso-olefin stream. Examples of suitable diluents include alkanes and straight chain olefins. The feed to the reactors, excluding alcohol, is generally diluted so as to include about 2 to about 80 weight percent iso-olefin, preferably about 10 to about 60 weight percent.

The acid ion-exchange catalysts useful in accordance with the present invention are relatively high molecular weight carbonaceous material containing at least one $-SO_3H$ functional group. These catalysts are exemplified by the sulfonated coals ("Zeo-Karb H", "Nalcite X" and "Nalcite AX") produced by the treatment of bituminous coals with sulfuric acid and commercially marketed as zeolitic water softeners or base exchangers. These materials are usually available in a neutralized form and in this case must be activated to the hydrogen form by treatment with a strong mineral acid such as hydrochloric acid and water washed to remove sodium and chloride ions prior to use. The sulfonated resin type catalysts are preferred for use in the present invention. These catalysts include the reaction products of phenol-formaldehyde resins with sulfuric acid ("Amberlite IR-1", "Amberlite IR-100" and "Nalcite MX"). Also useful are the sulfonated resinous polymers of coumaroneindene with cyclopentadiene, sulfonated polymers of coumarone-indene with cyclopentadience and furfural and sulfonated polymers of cyclopentadiene with furfural. The most preferred cationic exchange resins are strongly acidic exchange resins consisting essentially of sulfonated polystyrene resin, for instance, a divinylbenzene cross-linked polystyrene matrix having from 0.5 to 20 percent and preferably from 4 to 16 percent of copolymerized divinylbenzene therein to which are ionizable or functional nuclear sulfonic acid groups. These resins are manufactured and sold commercially under various trade names such as "Dowex 50", "Nalcite HCR" and "Amberlyst 15". As commercially obtained they have solvent contents of about 50 percent and can be used as is or the solvent can be removed first. The resin particle size is not particularly critical and therefore is chosen in accordance with the manipulative advantages associated with any particular size. Generally mesh sizes of 10 to 50 U.S. Sieve Series are preferred. The reaction may be carried out in either a stirred slurry reactor or in a fixed bed continuous flow reactor. The catalyst concentration in a stirred slurry reactor should be sufficient to provide the desired catalytic effect. Generally catalyst concentration should be 0.5 to 50 percent (dry basis) by weight of the reactor contents with from 1 to 25 percent being the preferred range.

Acid ion exchange resins, such as Amberlyst 15, are currently the most preferred catalyst for the etherification.

The temperature for the reaction zones and the space velocity for the feeds to the reactor zones can be selected as desired depending upon the degree of conversion desired and the temperature at which oligomerization becomes a problem. Generally, the temperature of the reaction zones will be in the range of about 30° C. to about 120° C., preferably about 35° C. to about 80° C. Pressures are generally selected to ensure that the charges and the products remain liquids during the reaction. Typical pressures are in the range of about 30 to about 300 psig. Generally, the liquid hourly space velocity (LHSV) of feed in the reactors will be in the range of about 5 to about 50 $hr^{-1}$, preferably about 5 to about 20 $hr^{-1}$.

The molar ratio of alcohol in said first feedstream to iso-olefin in said second feedstream will generally be in the range of about 0.5/1 to about 4/1, preferably about 0.8/1 to 1.2/1, most preferably about 1/1.

A preferred system for the present invention will now be described with reference to the accompanying drawing. An iso-olefin containing stream is passed from a source of supply via line 2 to a proportioning valve V1 which can vary the amount of said iso-olefin stream that can pass into lines 3 and 6. A feedstream containing alcohol is passed via line 1 to line 3. The combined stream from lines 1 and 3 are heated and passed to a first reactor R1 containing a bed of acid ion exchange resin. Effluent from reactor R1 is cooled and passed via line 5 to a reactor R2 also containing a bed of acid ion exchange resin. The cooling of the effluent is varied in response to the temperature of the total feed to reactor R2. Valve V1 is controlled in response to the temperature of the reactor R1 to vary the amount of the iso-olefin stream that is passed into line 3. The remainder of the iso-olefin stream is directed via line 6 to reactor R2. Effluent from reactor R2 is cooled and passed via line 7 to reactor R3 which also contains a bed of acid ion exchange resin.

In a preferred embodiment the iso-olefin stream would comprise isobutylene diluted with alkanes, n-alkenes, or mixtures thereof. Typically, the iso-olefin stream would contain about 10 to about 60 weight percent isobutylene with the remainder consisting essentially of alkanes and n-alkenes. The alcohol stream would consist essentially of methanol. The flow rates of the streams in lines 1 and 2 would preferably be such that the number of moles of methanol passing through line 1 is approximately equal to the number of moles of isobutylene passing through line 2. The combined streams of lines 1 and 3 would be heated to a temperature sufficient to give a desired degree of conversion in reactor R1. Typically, in reactor R1, it would be desirable to maintain temperatures in the range of about 50° to about 80° C., preferably with a maximum temperature no greater than about 75° C.

The valve V1 would be operated in response to the temperature of the bed in reactor R1 so as to direct more of the isobutylene stream to line 6 as the temperature rises. The directing of portions of the isobutylene stream to reactor R2 will reduce the amount of isobutylene present for reaction in the first reactor and will result in some reversible deactivation of the catalyst due to the leveling effect of the excess methanol. Thus the diverting of portions of the isobutylene stream to reactor R2 will result in a reduction in the heat buildup in reactor R1.

The effluent from reactor R1 would be cooled and combined with any of the diverted portions of the isobutylene containing stream. The combined streams could then be passed through reactor R2 for conversion of additional isobutylene to MTBE. Reactor R2 would also generally be operated at temperatures in the range of about 50° to about 80° C., preferably with a maximum temperature no greater than about 75° C. The cooling of the effluent from reactor R1 would be used to control the temperatures in reactor R2. The amount of cooling would be controlled in response to the temperature of the combined flows of lines 5 and 6.

Finally, the effluent from reactor R2 would be cooled and passed via line 7 to a polishing reactor R3. Since the concentration of isobutylene in line 7 would be small, reactor R3 would generally be operated at temperatures in the range of about 30° C. to about 60° C., preferably with a maximum temperature no greater than 45° C.

Effluent from reactor R3 can be recovered and separated as desired using conventional techniques.

The foregoing examples have been provided solely for the purpose of illustration. It will be apparent to those skilled in the art that various modifications can be made without departing from the spirit or scope of the invention. For example, the diversion of isobutylene from the first reactor to the second need not be relied upon solely for control of the temperature in the first reactor. Varying the heating of the feed to the reactor could also assist. The invention is accordingly also applicable to those systems using additional means to control reactor temperature, for example, effluent recycle.

What is claimed is:

1. In a process for producing aliphatic ether wherein a first feedstream comprising at least one alcohol selected from the group consisting of primary and secondary aliphatic alcohols containing 1 to 12 carbon atoms and a second feedstream comprising at least one iso-olefin having 4 to 6 carbon atoms are passed through a first reaction zone containing an acid ion exchange resin under conditions such that iso-olefin is converted to aliphatic ether and effluent from said first reaction zone is passed through a second reaction zone containing an acid ion exchange resin under conditions such that iso-olefin is converted to aliphatic ether, the improvement comprising diverting portions of said second feedstream to said second reaction zone in response to the temperature of said first reactor as required to assist in maintaining the maximum temperature in said first reaction zone below a selected value.

2. A process according to claim 1 wherein isobutylene is the predominate iso-olefin in said second feedstream and methanol is the predominate alcohol in said first feedstream.

3. A process according to claim 2 wherein the temperature of said first reaction zone is maintained in the range of about 50° C. to about 80° C.

4. A process according to claim 3 wherein the temperature of said second reaction zone is maintained in the range of about 50° C. to about 80° C.

5. A process according to claim 4 wherein the maximum temperature in said first reaction zone is no greater than about 75° C.

6. A process according to claim 5 wherein the liquid hourly space velocity of feed to said first and second reaction zones is in the range of about 5 to about 20 $hr^{-1}$.

7. A process according to claim 6 wherein the molar ratio of methanol in said first feedstream to isobutylene in said second feedstream is about 1/1.

8. A process according to claim 7 wherein effluent from said second reaction zone is passed through a third reaction zone containing an acid ion exchange resin under conditions such that isobutylene is converted to aliphatic ether, said third reaction zone being maintained at temperatures in the range of about 30° C. to about 60° C.

9. A process according to claim 8 wherein the maximum temperature in said third reaction zone is no greater than about 45° C.

10. A process according to claim 9 wherein said iso-olefin consists essentially of isobutylene and said alcohol consists essentially of methanol.

11. A process according to claim 10 wherein said acid ion exchange resin is present in said first, second, and third reaction zones in the form of fixed beds.

12. A process according to claim 7 wherein said iso-olefin consists essentially of isobutylene and said alcohol consists essentially of methanol.

13. A process according to claim 7 wherein said acid ion exchange resin is present in said first and second reaction zones in the form of fixed beds.

14. A process according to claim 7 wherein said second feedstream contains about 10 to about 60 weight percent iso-olefin.

15. A process according to claim 11 wherein said second feedstream contains about 10 to about 60 weight percent isobutylene.

* * * * *